(12) United States Patent
Hsieh et al.

(10) Patent No.: US 11,185,610 B2
(45) Date of Patent: Nov. 30, 2021

(54) PREPARATION OF ACELLULAR CARTILAGE GRAFT AND USES THEREOF (71) Applicant: Acro Biomedical Company. Ltd., Kaohsiung (TW)

(72) Inventors: Dar-Jen Hsieh, Kaohsiung (TW); Ming-Yao Chang, Kaohsiung (TW)

(73) Assignee: ACRO BIOMEDICAL COMPANY. LTD., Kaohsiung (TW)

( * ) Notice: Subject to any disclaimer, the term of this patent is extended or adjusted under 35 U.S.C. 154(b) by 556 days.

(21) Appl. No.: 15/739,164

(22) PCT Filed: Aug. 11, 2016

(86) PCT No.: PCT/CN2016/094633
§ 371 (c)(1),
(2) Date: Dec. 22, 2017

(87) PCT Pub. No.: WO2017/025053
PCT Pub. Date: Feb. 16, 2017

(65) Prior Publication Data
US 2018/0369449 A1  Dec. 27, 2018

Related U.S. Application Data (60) Provisional application No. 62/203,904, filed on Aug. 11, 2015.

(51) Int. Cl.
*A61L 15/00* (2006.01)
*C07K 14/78* (2006.01)
(Continued)

(52) U.S. Cl.
CPC .......... *A61L 27/3612* (2013.01); *A61L 27/20* (2013.01); *A61L 27/24* (2013.01); *A61L 27/362* (2013.01);
(Continued)

(58) Field of Classification Search
CPC ............ A61L 27/3612; A61L 27/3654; A61L 27/3687; A61L 27/3691; A61L 27/362; A61L 27/20; A61L 27/24; A61L 27/52; A61L 2430/40; A61L 2400/06; A61L 2430/34; A61L 2400/12; A61L 2430/06; A61L 27/3683; C07K 1/36; C07K 14/78
See application file for complete search history.

(56) References Cited

U.S. PATENT DOCUMENTS

| | | | |
|---|---|---|---|
| 2003/0072677 A1* | 4/2003 | Kafesjian | A61L 27/3604 422/33 |
| 2011/0046732 A1* | 2/2011 | Dyke | A61K 35/34 623/13.11 |
| 2012/0100225 A1* | 4/2012 | McKay | A61L 27/54 424/549 |

FOREIGN PATENT DOCUMENTS

WO  WO-2012141454 A2 * 10/2012  ......... A61L 27/3654

* cited by examiner

*Primary Examiner* — Marcia S Noble
*Assistant Examiner* — Lauren K Van Buren

(57) ABSTRACT

Disclosed herein is a method of producing acellular cartilage grafts. The method includes steps of, subjecting a cartilage matrix derived from an animal to alkaline, disinfection and decelluarization treatments. The thus produced cartilage graft is devoid of any cellular matters, while maintaining the porosity and integrity of collagen fibers therein, thus is suitable as a xenograft for host cells to grown thereon. Also disclosed herein is a method for treating osteochondral disease of a subject, in which the present acellular cartilage graft is applied to a lesion site of the subject.

10 Claims, 5 Drawing Sheets

(A)

(B)

(C)

(D)

(51) Int. Cl.
*A61L 27/24* (2006.01)
*A61L 27/56* (2006.01)
*A61L 27/36* (2006.01)
*C07K 1/36* (2006.01)
*A61L 27/20* (2006.01)
*A61L 27/52* (2006.01)

(52) U.S. Cl.
CPC ....... *A61L 27/3654* (2013.01); *A61L 27/3687* (2013.01); *A61L 27/3691* (2013.01); *A61L 27/52* (2013.01); *C07K 1/36* (2013.01); *C07K 14/78* (2013.01); *A61L 2400/06* (2013.01); *A61L 2400/12* (2013.01); *A61L 2430/06* (2013.01); *A61L 2430/34* (2013.01); *A61L 2430/40* (2013.01)

PREPARATION OF ACELLULAR CARTILAGE GRAFT AND USES THEREOF

CROSS-REFERENCE TO RELATED APPLICATIONS

This application is a U.S. National Stage Filing under 35 U.S.C. 371 from International Patent Application Serial No. PCT/CN2016/094633, filed Aug. 11, 2016, and published on Feb. 16, 2017, which claims the priority of U.S. Ser. No. 62/203,904, filed Aug. 11, 2015, the disclosure of which are incorporated by reference herein in their entireties.

BACKGROUND OF THE INVENTION

1. Field of the Invention

The present disclosure in general relates to the field of producing acellular cartilage graft, particularly, improved methods for producing acellular cartilage grafts suitable for use as a biological scaffold for cells to grow thereon, thus the acellular cartilage grafts are useful as xenografts for the treatment of osteochondral diseases.

2. Description of Related Art

Damage to cartilage tissue is quite common in active individuals and elder population as a result of acute or repetitive injury or aging. Treatment options include rest, minor arthroscopic surgery to clean up the damaged cartilage area, and other surgical procedures such as microfracture, drilling, and abrasion. All of these provide only symptomatic relief, with temporary benefit, especially if the person maintained the same level of activities before the injury. For example, chronic knee joint cartilage damage may lead to greater deterioration of the joint cartilage and may eventually lead to a total knee joint replacement. Osteochondral disease or injuries present another challenge, for which treatment needs have not been fully met by the currently medical procedures and methods. In addition to cartilage damage resulted from aging, injury and/or disorders as described above, there is also an increasing need of cartilage graft in plastic or cosmetic surgery that requires repair or augmentation of cartilaginous tissue, such as nasal augmentation, corrective surgery for facial left-right asymmetry, corrective surgery around eyelids, cosmetic surgery of face, and the like.

Existing engineered cartilage generated by seeding a hydrogel or a natural or synthetic polymeric scaffold does not possess the same mechanical properties of a nature cartilage, in which collagen is the main component. To overcome such drawback, cross-linkers, such as glutaraldehyde, have been used to improve the mechanical strength of the hydrogel or polymeric scaffold. However, the cross-linkers are mostly toxic to human, thus their uses are limited.

Accordingly, it would be advantageous to provide an improved cartilage graft for treatment to any injuries or corrective surgery described above. The improved cartilage graft would not only possess the mechanical strength and conformation of a nature cartilage, thus may effectively restore the cartilage to its pre-injury state without causing further complications (e.g., immunogenicity issue); but also is easy to prepare at a relatively low cost.

SUMMARY

The present disclosure was created by the present inventors to overcome the above-noted problems in the production of an improved cartilage graft, especially in the production of the cartilage graft characterized in having improved mechanical strength, and native conformation of a natural cartilage.

Accordingly, it is the first aspect of this disclosure to provide a method for preparing an acellular cartilage graft suitable for use in cosmetic surgery (e.g., rhinoplasty, corrective surgery of face and etc.) or for the treatment of osteochondral diseases. The method includes steps of, (1) dicing a cartilage of an animal to produce a cartilage matrix;

(2) subjecting the cartilage matrix of the step (1) to an alkaline treatment;

(3) subjecting the alkaline treated cartilage matrix of the step (2) to a disinfection treatment; and (4) subjecting the disinfected cartilage matrix of the step (3) to a decellularization treatment to produce the acellular cartilage graft.

According to embodiments of the present disclosure, in the step (1), the cartilage is derived from a mammal, and may be a nasal cartilage, a rib cartilage, an ear cartilage, or a knee cartilage.

According to embodiments of the present disclosure, in the step (2), the alkaline treatment comprises treating the cartilage matrix with a sodium hydroxide solution at room temperature for about 3-24 hours.

According to embodiments of the present disclosure, in the step (3), the alkaline treated cartilage matrix was subjected to treatment of a disinfectant, which may be selected from the group consisting of, an alcohol, an oxidizing agent, a radiation, a phenolic, and a quaternary ammonium compound.

In some embodiments, in the step (3), the alkaline treated cartilage matrix was subjected to the treatment of an alcohol, which may be ethanol or isopropanol.

In further embodiments, in the step (3), the alkaline treated cartilage matrix was subjected to the treatment of an oxidizing agent, which may be hydrogen peroxide.

In still further embodiments, in the step (3), the alkaline treated cartilage matrix was subjected to the treatment of a radiation, which may be a gamma ray.

In other embodiments, in the step (3), the alkaline treated cartilage matrix was subjected to the treatment of a phenolic, which may be paraben, benzoic acid, or salicylic acid.

In still further embodiments, in the step (3), the alkaline treated cartilage matrix was subjected to the treatment of a quaternary ammonium compound, which may be benzalkonium chloride, alkyldimethylbenzylammonium chloride, didecyldimethylammonium chloride, or ammonium chloride.

According to embodiments of the present disclosure, in the step (4), the decellularization treatment comprises subjecting the disinfected cartilage matrix to a supercritical fluid (SCF) under a pressure of about 150-350 bar at a temperature between 30-50° C. for about 20 min to 5 days.

The SCF may be any of a supercritical carbon dioxide ($scCO_2$), a supercritical nitrous oxide ($scN_2O$), a supercritical water ($scH_2O$), a supercritical alkane, a supercritical alkene, a supercritical alcohol or a supercritical acetone. In one example, the SCF is $scCO_2$. In another example, the SCF is $scN_2O$.

According to one preferred embodiment, the decellularization treatment is carried out at a condition, in which the temperature is about 37° C., the pressure is about 350 Bar, and the treatment was performed for 100 mins.

The thus produced cartilage graft is mainly constituted by collagens, in which their native structures and conformations are preserved, so that they may serve as a three-dimensional bio-scaffold that allows cells to grow thereon after being applied to a subject (e.g., implantation). Further, the thus produced cartilage graft is acellular, meaning it is devoid of any cellular matters, thus is substantially non-immunogenic and will not induce any immunogenic response to its host. In addition, the mechanical property of the thus produced cartilage graft is superior to that of a native cartilage, rendering it a better xenograft over the native cartilage and/or the existing engineered cartilage.

Accordingly, it is the second aspect of this disclosure to provide a cartilage graft prepared by the present method. The cartilage graft of the present disclosure is thus useful as a xenograft in corrective surgery or for treating cartilage defects resulted from aging, injury, or disease. Examples of the corrective surgery include, but are not limited to, nasal augmentation, corrective surgery for facial left-right asymmetry, corrective surgery around eyelids, cosmetic surgery of face, and the like.

It is the third aspect of this disclosure to provide a method for treating osteochondral diseases. The method includes applying the present acellular cartilage graft to a treatment site (e.g., a lesion site) of the subject.

The osteochondral diseases may be, congenital defects, bone fractures, meniscal injuries or defects, bone/spinal deformation, osteosarcoma, myeloma, bone dysplasia and scoliosis, osteoporosis, periodontal disease, dental bone loss, osteomalacia, rickets, fibrous osteitis, renal bone dystrophy, spinal fusion, spinal disc reconstruction or removal, Paget's disease of bone, meniscal injuries, rheumatoid arthritis, osteoarthritis, and a traumatic or surgical injury to cartilage.

The details of one or more embodiments of this disclosure are set forth in the accompanying description below. Other features and advantages of the invention will be apparent from the detail descriptions, and from claims.

It is to be understood that both the foregoing general description and the following detailed description are by examples, and are intended to provide further explanation of the invention as claimed.

BRIEF DESCRIPTION OF THE DRAWINGS

The accompanying drawings, which are incorporated in and constitute a part of the specification, illustrate various example systems, methods and other exemplified embodiments of various aspects of the invention. The present description will be better understood from the following detailed description read in light of the accompanying drawings, where, FIG. 1 are photographs of the present cartilage graft by H&E staining (A) before, and after SCF treatment at $(B)_{150}$ bar, (C) 200 bar, and (D) 350 bar taken at a magnification of 20,000× in accordance with one embodiment of the present disclosure.

DETAILED DESCRIPTION OF THE PREFERRED EMBODIMENTS

The detailed description provided below in connection with the appended drawings is intended as a description of the present disclosure and is not intended to represent the only forms in which the present disclosure may be constructed or utilized.

The singular forms "a", "and", and "the" are used herein to include plural referents unless the context clearly dictates otherwise.

The term "acellular" as used herein refers to an implant that is free of any cellular matters, such as biologically active cells and/or debris thereof. Accordingly, the term "acellular cartilage graft" refers to a cartilage graft derived from a cartilage of an animal (e.g., a mammal) that is substantially free of any cellular matters. In one example, the cartilage is taken from the nasal cartilage of a hog. In another example, the cartilage is taken from the knee cartilage of a hog. In a further example, the cartilage is derived from a rib cartilage of a hog.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

The present disclosure, in its broadest term, pertains to the preparation of an acellular cartilage graft, which is suitable for use in a cosmetic or plastic surgery; or for the treatment of osteochondral diseases, which include repair or restoration of damaged, injured, traumatized or aged cartilage and/or repair of osteochondral defects, by implanting an acellular cartilage graft produced by the present method into the cartilage lesion.

Accordingly, the objective of the present disclosure is directed to a method of producing an acellular cartilage graft, in which the mechanical strength, and native structure and conformation of collagen are preserved, thus may provide an optimal micro-environment for host tissue cells to grow thereon once the present acellular cartilage graft is implanted into the host for tissue reconstruction or for the treatment of osteochondral diseases. Further, the cartilage graft produced by the present method is devoid of any cellular matters, thus is substantially non-immunogenic and will not induce any immunogenic response after implantation.

Accordingly, the present method includes at least, the following steps, (1) dicing a cartilage of an animal to produce a plurality of cartilage matrices;

(2) subjecting the cartilage matrices of the step (1) to an alkaline treatment;

(3) subjecting the alkaline treated cartilage matrices of the step (2) to a disinfection treatment; and (4) subjecting the disinfected cartilage matrices of the step (3) to a decellularization treatment to produce the acellular cartilage grafts.

To produce the desired acellular cartilage graft, an intact cartilage such as a nasal cartilage, a rib cartilage, an ear cartilage or a knee cartilage is removed from a non-human animal, preferably from a farm animal, and use as the source of cartilage. Examples of suitable farm animals that may act as the source of cartilage include, but are not limited to, hogs, cattle, cows, bulls, sheep, goats, donkeys, rabbits, ducks, geese, and fowls. The cartilage, which serves as the source of the cartilage graft should preferably be collected from freshly killed animals, and immediately placed in sterile isotonic solution or other preserving solution. The harvested cartilage is then cut into suitable sizes and shapes, thereby producing cartilage matrices that are shape as discs, strips, particles, and cones. In some examples, each cartilage matrices has the shape of a disc, and is about 8-12 mm in diameter, preferably about 11 mm in diameter. In other examples, each cartilage matrices has the shape of a strip that is about 6 cm in length, 10 mm in width, and 2-5 mm in thickness. In general, the size and shape of each cartilage graft are not critical in accordance with the present disclosure, so long as it complies with the size and shape of the treatment site.

The diced cartilage matrices are then subjected to alkaline treatment and disinfection treatment as described in the steps (2) and (3), respectively. Examples of alkaline agent suitable for used in the present method include, but are not limited to, sodium hydroxide, potassium hydroxide, calcium hydroxide, urea, sodium sulfide, calcium thioacetate and etc. Preferably, the cartilage matrices are treated with a sodium hydroxide solution at room temperature for about 3 hrs. Disinfection may be carried out by subjecting the cartilage matrices to the treatment of a disinfection agent, such as an alcohol, an oxidizing agent, a phenolic compound, a quaternary ammonium compound, antibiotic, and radiation, to sterilize the cartilage matrices. Suitable examples of disinfection agent useful for the present method include, but are not limited to, ethanol, isopropanol, sodium bicarbonate, hydrogen peroxide, acetic acid, sulfonamides, paraben, benzoic acid, salicylic acid, benzalkonium chloride, alkyldimethylbenzylammonium chloride, didecyldimethylammonium chloride, ammonium chloride, X-ray, gamma radiation, and UV light. In some embodiment, the cartilage matrices are treated with hydrogen peroxide solution. Further, after each steps, the cartilage matrices are washed with copious amounts of water to remove any soluble matters, before being subjected to the next treatment.

Next, the alkaline-treated, disinfected cartilage matrices of the step (3) are subjected to a decellularization process. The decellularization process is performed for the purpose of removing the cellular materials from the cartilage tissue, while preserving the physical and biochemical properties of collagen, so that it may better serve as a tissue scaffold (e.g., a xenograft). Accordingly, in step (4), the disinfected cartilage matrices of step (3) are treated with a supercritical fluid (SCF) under a pressure of about 100-500 bar, such as 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490 and 500 bar; preferably about 150-350 bar, such as 150, 160, 170, 180, 190, 200, 210, 220, 230, 240, 250, 260, 270, 280, 290, 300, 310, 320, 330, 340, and 350 Bar. Further, the step (4) is performed at a temperature between 30-50° C., such as 30, 31, 32, 34, 35, 36, 37, 38, 39, 40, 41, 42, 43, 44, 45, 46, 47, 48, 49 and 50° C.; preferably between 35-45° C., such as 35, 36, 37, 38, 39, 40, 41, 42, 43, 44, and 45° C.; for about 20 min to 5 days, such as 20, 30, 40, 50, and 60 mins; 2, 3, 4, 5, 6, 7, 8, 9, 10, 11, 12, 13, 14, 15, 16, 17, 18, 19, 20, 21, 22, 23, and 24 hrs; 2, 3, 4, and 5 days. In some examples, the disinfected cartilage matrices of step (3) are treated with SCF for about 1 to 24 hrs. In other examples, the disinfected cartilage matrices of step (3) are treated with SCF for about 2 to 5 days.

The SCF may be any of a supercritical carbon dioxide ($scCO_2$), a supercritical nitrous oxide ($scN_2O$), a supercritical water ($scH_2O$), a supercritical alkane, a supercritical alkene, a supercritical alcohol or a supercritical acetone. In one example, the SCF is $scCO_2$, for $scCO_2$ has mild critical condition of 37° C. at about 350 Bar, hence allows biological materials to be removed at or near body temperature (i.e., 37° C.). In another preferred example, the SCF is $scN_2O$.

Optionally, the SCF is applied is applied to the disinfected cartilage matrices of step (3) along with a co-solvent. The co-solvent may be a $C_{1-4}$ alcohol, which includes but is not limited to, ethanol, propanol, isopropanol, butanol, isobutanol, sec-butanol, t-butanol, and cyclobutanol. In some preferred examples, the co-solvent is ethanol, and is applied along with SCF in a volume ratio of 1:20 to 1:4, such as 1:20, 1:19, 1:18, 1:17, 1:16, 1:15, 1:14, 1:13, 1:10, 1:9, 1:8, 1:7, 1:6, 1:5, and 1:4. In one preferred embodiment, the ethanol is applied with SCF in a volume ration of 1:19. In another embodiment, the ethanol is applied with SCF in the volume ratio of 1:10. In still another embodiment, the ethanol is applied with SCF in the volume ratio of 1:4. Most preferably, the ethanol and SCF are applied simultaneously at the volume ratio of about 1:10.

According to embodiments of the present disclosure, the SCF treated cartilage grafts of step (4) are substantially devoid of any cellular matters, thus do not require any additional enzyme digestion treatment (e.g., digestion with protease, and/or glycosidase) to remove antigenic surface carbohydrate moieties that might serve as a source of immunogenic rejection of a xenograft. According to embodiments of the present disclosure, the cartilage grafts produced by the present method are devoid of any nucleic acids, and non-collagen proteins.

Further, the SCF treated cartilage grafts of step (4) is constituted by collagen fibers in which the mechanical strength and integrity of the collagen fibers are maintained, thus, they are suitable for use as biological scaffolds for host cells to grow thereon. According to embodiments of the present disclosure, the cartilage grafts of the present disclosure preserve the native structure and conformation of collagen fibers, and are capable of supporting the growth of fibroblast cells.

It is worth noting that the present method differs from the prior art method in that, the conventional use of hypertonic salt solution, de-watering and/or freezing treatments for the preparation of a cartilage graft are eliminated, rendering the present method more simplified and easy to use, while maintaining the integrity and/or mechanical strength of the collagen fibers in the produced cartilage graft. Further, the present method differs from the prior art method in that, it does not require the use of a cross-linking agent (e.g., glutaraldehyde, formaldehyde, and the like) to crosslink the proteins of the cartilage grafts, so that toxicity and immunogenicity of the cartilage grafts are reduced or diminished.

According to optional embodiments of the present disclosure, the SCF treated cartilage grafts may be sterilized using any known method (e.g., treatment with a disinfection agent as described previously) and stored at a desiccated, and sterilized condition until use. In some embodiments, the cartilage grafts are exposed to gamma ray with an intensity of 10-60 kGy, such as 10, 20, 30, 40, 50, and 60 kGy, to sterilize the cartilage grafts. More preferably, the cartilage grafts are exposed to gamma ray with an intensity of 10-30 kGy, such as 10, 15, 20, 25, and 30 kGy to sterilize the cartilage grafts.

The acellular cartilage graft thus produced are suitable for use in a cosmetic or plastic surgery; or for the treatment of osteochondral diseases, which include reconstruct, repair or restoration of damaged, injured, traumatized or aged cartilage and/or repair of osteochondral defects, by implanting an acellular cartilage graft produced by the present method into the treatment site (e.g., cartilage lesion).

It is therefore a further aspect of the present disclosure to provide a method of treating osteochondral diseases of a subject. The method comprises the step of, applying the present cartilage grafts to a treatment site (e.g., a lesion site) of the subject. Examples of the osteochondral diseases include, for example but are not limited to, congenital defects, bone fractures, meniscal injuries or defects, bone/spinal deformation, osteosarcoma, myeloma, bone dysplasia and scoliosis, osteoporosis, periodontal disease, dental bone loss, osteomalacia, rickets, fibrous osteitis, renal bone dystrophy, spinal fusion, spinal disc reconstruction or removal, Paget's disease of bone, meniscal injuries, rheumatoid arthritis, osteoarthritis, or a traumatic or surgical injury to cartilage. It is envisioned that after the present SCF treated cartilage graft is implanted into the lesion site, neighboring chondrocytes would be activated and move into the porous structure of the cartilage graft where they begin to grow until ultimately replacing the damaged cartilage in the lesion site, and the present SCF treated cartilage graft is completely degraded leaving no toxic residues in the subject.

The present invention will now be described more specifically with reference to the following embodiments, which are provided for the purpose of demonstration rather than limitation. While they are typically of those that might be used, other procedures, methodologies, or techniques known to those skilled in the art may alternatively be used.

EXAMPLES

Materials and Methods
Cell Cultures
NIH-3T3 fibroblast cells were cultured in DMEM-high glucose with supplements, including 10% fetal bovine serum (FBS), 100 units/ml penicillin and 100 mg/ml streptomycin at 37° C. in a humidified atmosphere with 5% CO2.

Isolation of Chondrocytes
Chondrocyte were isolated from porcine articular cartilage. The cartilage was rinsed in culture medium and then transferred to a digestion medium (DMEM, 10% FBS, 1% P/S, 0.1 mg/mL streptomycin) containing collagenase type H and incubated for 24 hr at 37° C. Cell were collected by centrifugation (300×g for 5 min).

H & E Staining
The cartilage tissue sectioned was deparaffinized by immersing in xylene for 10 min, and the treatment was repeated once. The deparaffinized tissue was then hydrated by passing through a series of alcohol bath, in which the alcohol concentration varied from 100%, to 95%, 85%, and 75%, respectively. In each pass, the tissue sample was allowed to stay in the alcohol solutions for 2 min, then rinsed with copious amount of deionized water. After hydration, the tissue sample was stained with hematoxylin for 3-5 minutes, then washed with de-ionized water and 75% ethanol. The hematoxylin stained cartilage was further stained with 1% Eosin Y for about 30 sec, followed by wash with deionized water, and 95% and 100% ethanol, sequentially.

Alcian Blue Staining
The cartilage tissue section was deparaffinized and hydrated in accordance with procedures described in the "H & E staining" section. Then, the sample was stained with alcian blue for 30 mins, followed by washing in running tap water for 2 mins, and rinsing with deionized water. The alcian blue stained cartilage sample was counterstained in nuclear fast red solution for 5 mins, then washed in running tap water for 1 min. The cartilage sample was then dehydrated by passing through 95% ethanol, and 100% ethanol (twice, each time for 2 mins), then mounted with resinous mounting medium.

Recellularization of 3T3 Cells on the Cartilage Grafts
3T3 cells were grown to 80% confluent, then harvested by enzyme treatment (0.25% trypsin in 1 mM EDTA), and centrifugation at 500×g for 5 min. The collected cells were re-suspended in culture medium to a final concentration of $2 \times 10^6$ cells/mL. The present SCF-treated cartilage grafts were pre-wetted with culture medium and incubated overnight, then were placed into low-attachment 24-well plates (Corning). Half of the cell suspension (200 uL) was carefully placed onto one side of each SCF-treated cartilage grafts, and cultured for 2 hours in the incubator to ensure cells were attached onto the surface. The remaining cell suspension was placed onto the other side (i.e., the side that had not being in contact with cells) of the SCF-treated cartilage grafts in accordance with the same method just described. Each cell seeded cartilage grafts were then cultured in 2 mL culture medium for 7 days, and then fixed in 10% formalin for the following analysis.

Recellularization of Primary Chondrocytes on the Cartilage Grafts
The cartilage grafts were placed in 24-well plate (200 mg/well), then freshly isolated chondrocytes were seeded onto the cartilage grafts. The final cell number was $1.2 \times 10^7$ cells per well in culture medium. The medium was changed three times a week. After 2 weeks in culture, the cartilage grafts were collected, and then fixed in 10% formalin for subsequent analysis.

Measurement of Compressive Strength
All cartilage samples were rehydrated in PBS solution for at least 16 hours, then the respective heights and/or diameters, depended on the shapes of the samples, were measured; if the cartilage sample was in the shape of a strip, then its height was measured; on the other hand, if the cartilage sample was in the shape of a disc, then its diameter before the test was recorded. The compressive strength measurement was carried out in Lloyd machine (LRX Instrument, England). Each tests started with a preload of 2N, and the loading speed was set to be 0.18 mm/min, the test was aborted when the load resulted in 65% drop of the sample height and/or diameter.

Example 1 Preparation and Characterization of the Cartilage Grafts 1.1 Preparation of the Decellularized Cartilage Grafts Porcine joints were sterilized and the cartilage was surgically removed. The cartilage was washed with water, and then diced into matrices of various sizes and shapes according to the intended applications.

The cartilage matrices were first immersed in sodium hydroxide solution (1N) for 3 hrs at room temperature, then in hydrogen peroxide solution (5%) at 4° C. for 48 hrs. After each solution treatments, the cartilage matrices were washed with copious amounts of water to remove any residual treatment solution.

Then, the cartilage matrices were subjected to treatment of $scCO_2$ at 350 Bar, 37° C. for 100 min to remove any residual cellular matters and thereby generated the decellularized cartilage grafts, which were irradiated with gamma ray (30 kGy) and stored at a desiccated, and sterilized condition until use.

1.2 Characterization of the cartilage grafts of example 1.1

Figure 1:
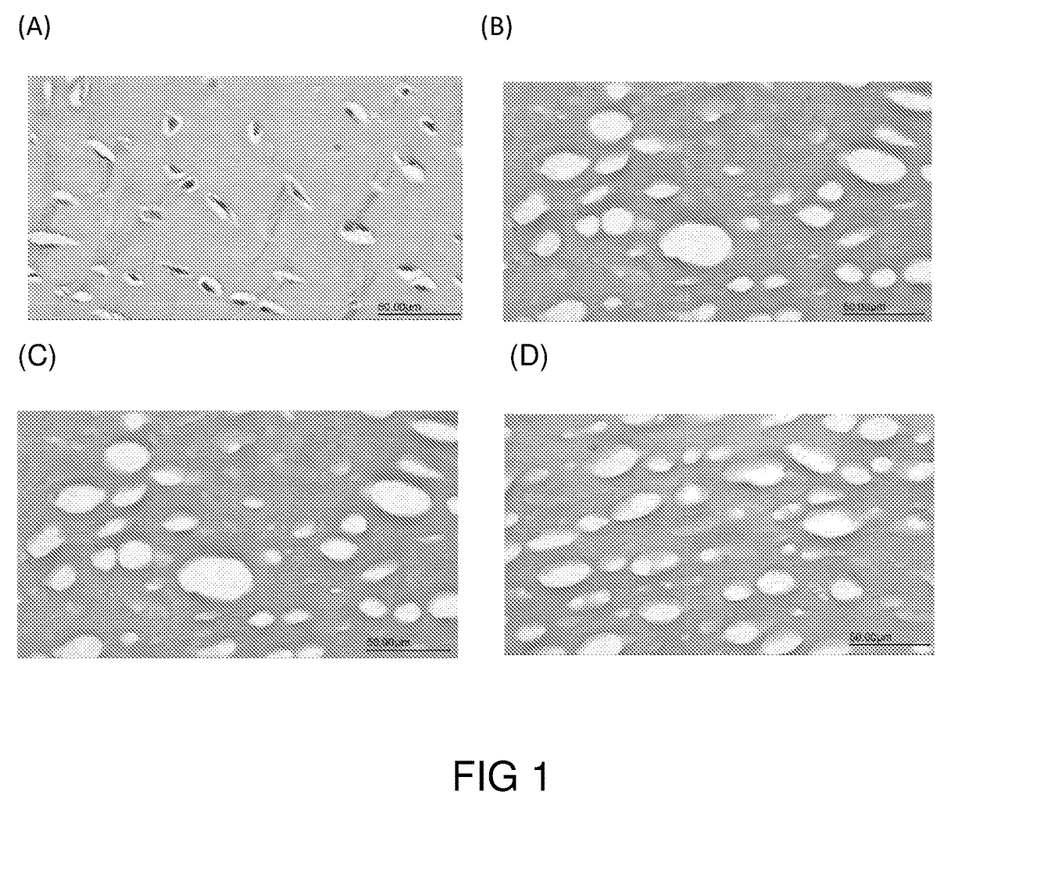
Figure 2:
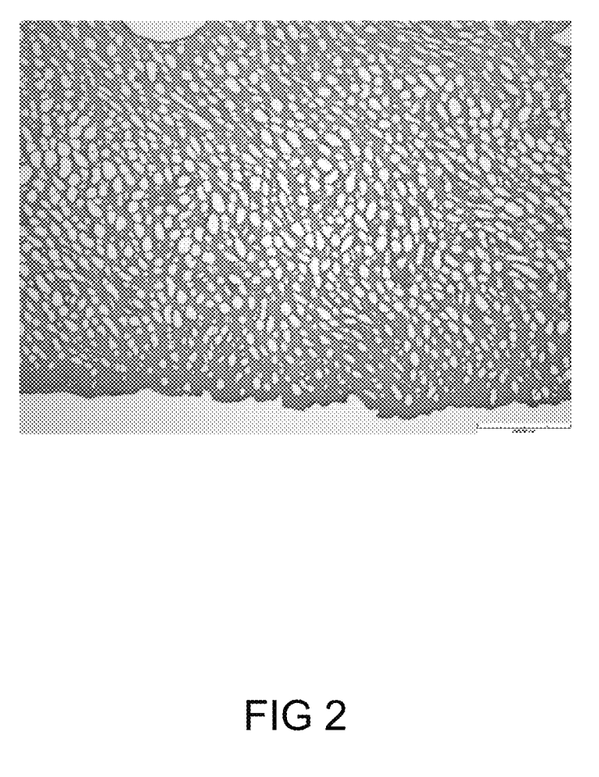
FIG. 2 is a photograph of H&E staining of the present cartilage graft after SCF treatment in accordance with one embodiment of the present disclosure.
Figure 3:
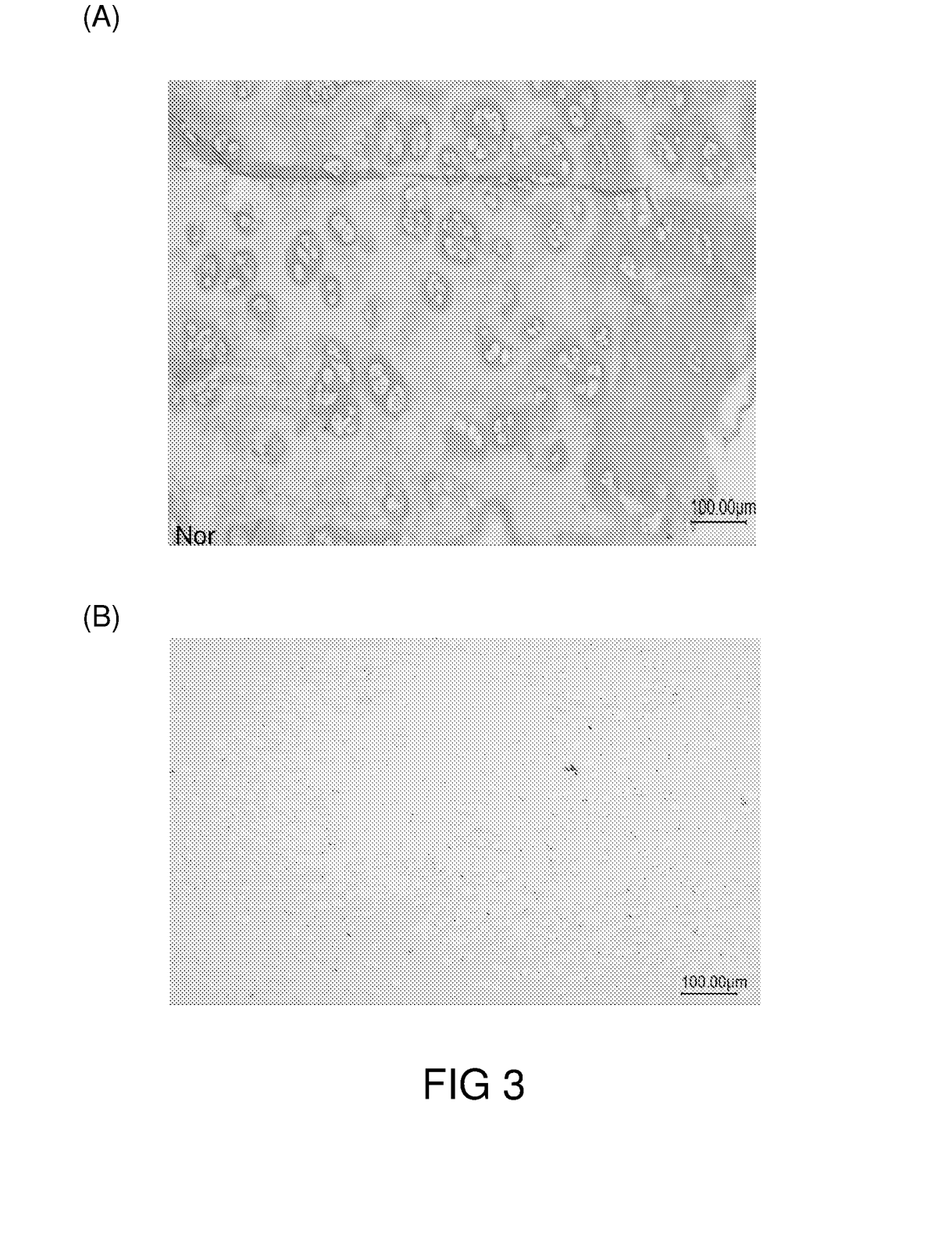
FIG. 3 are photographs of alcian blue staining of the present cartilage graft (A) before, and (B) after SCF treatment in accordance with one embodiment of the present disclosure.

The morphology analysis indicated that, prior to the SCF treatment, residual cellular matters were observed in the lacuna, a small space containing chondrocytes in cartilage (FIG. 1, panel A); however, after SCF treatment at various levels of pressure, the residual cellular matters previously observed at lacuna, vanished completely (FIG. 1, panels B, C, and D), which confirmed that SCF treatment was an effective means for removing cellular matters from cartilage. The results were further confirmed by H&E staining, DAPI and alcian blue staining, in which neither the cell nuclei (FIG. 2), nor the acidic polysaccharides (e.g., glycosaminoglycans in cartilage) (FIG. 3) were positively stained. Taken together, results from FIGS. 1 to 3 confirmed that no residual cellular matters (e.g., nuclei, and carbohydrate moieties) were present in the SCF treated cartilage grafts.

Figure 4:
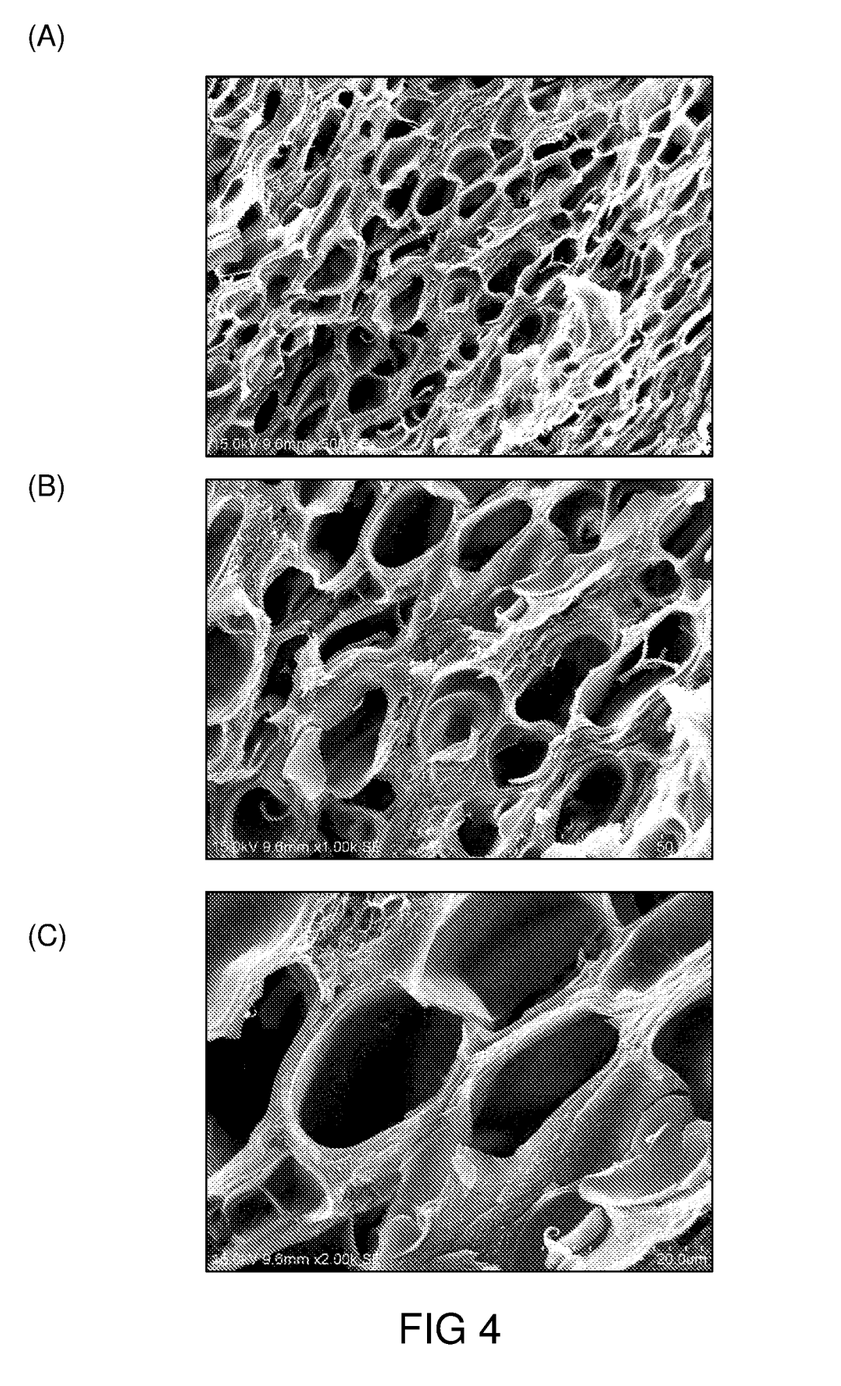
FIG. 4 are scanning electronic microscopy (SEM) photographs of the present SCF treated cartilage graft taken at a magnification of (A) 500 k, (B) 1000 k and (C) 2,000 k in accordance with one embodiment of the present disclosure.

Further, the porosity of the SCF treated cartilage grafts remained relatively intact (FIG. 4), lending support for recellularizing 3T3 cells as well as primary chondrocytes thereon, in which primary chondrocytes were observed to migrate into the porous structure of cartilage grafts of example 1.1 and embedded in the lacuna (data not shown).

Figure 5:
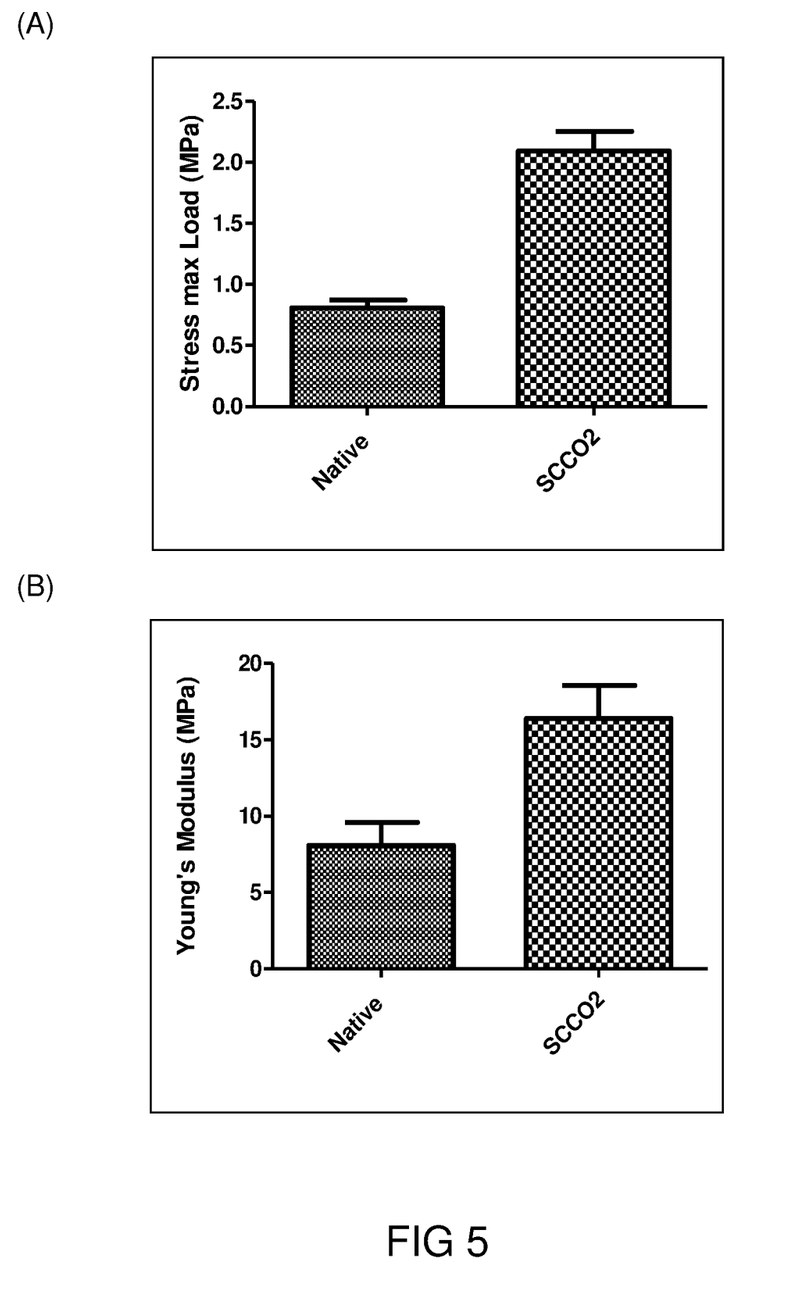
FIG. 5 are bar graphs depicting the compressive strengths of the present SCF treated cartilage graft of example 1.1 and the native cartilage respectively presented in (A) stress load, and (B) Young's modulus in accordance with one embodiment of the present disclosure.

The mechanical property of the SCF treated cartilage graft of example 1.1 was superior than that of a native cartilage, in which the SCF treated cartilage graft of example 1.1 could withstand at least 2 folds of stress in a compression test (FIG. 5).

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of the present disclosure.

What is claimed is:

1. A method for preparing acellular cartilage grafts consisting essentially of:
   (1) dicing a cartilage of an animal to produce a plurality of cartilage matrices;
   (2) treating the cartilage matrices of the step (1) with a sodium hydroxide solution at room temperature for about 3-24 hours;
   (3) disinfecting the cartilage matrices of the step (2) with a disinfection agent selected from the group consisting of an alcohol, an oxidizing agent, a radiation, a phenolic compound, and a quaternary ammonium compound; and
   (4) decellularizing the disinfected cartilage matrices of the step (3) in a supercritical fluid (SCF) to produce the disinfected acellular cartilage grafts, wherein the decellularization is conducted under a pressure of about 150-350 bar at a temperature between 30-50° C. for about 100 minutes,
   wherein the method is free of the use of enzymatic digestion, hypertonic salt solution, de-watering treatment, freezing treatment, and cross-linking agent.

2. The method of claim 1, wherein the cartilage is a nasal cartilage, a rib cartilage, an ear cartilage, or the knee cartilage obtained from a hog.

3. The method of claim 2, wherein each cartilage graft is shaped as a disc, a strip, a cone, or a particle.

4. The method of claim 1, wherein the alcohol is ethanol or isopropanol.

5. The method of claim 1, wherein the oxidizing agent is hydrogen peroxide.

6. The method of claim 1, wherein the phenolic compound is paraben, benzoic acid, or salicylic acid.

7. The method of claim 1, wherein the quaternary ammonium compound is benzalkonium chloride, alkyldimethylbenzylammonium chloride, didecyldimethylammonium chloride, or ammonium chloride.

8. The method of claim 1, wherein the SCF is and/or a supercritical carbon dioxide ($scCO_2$), a supercritical nitrous oxide ($scN_2O$), a supercritical water ($scH_2O$), a supercritical alkane, a supercritical alkene, a supercritical alcohol and/or a supercritical acetone.

9. The method of claim 8, wherein the SCF is $scCO_2$, the temperature is about 37° C., and the pressure is about 350 Bar.

10. The method of claim 9, wherein each of the acellular cartilage grafts can withstand at least two folds of stress than that of a native cartilage.

* * * * *